United States Patent [19]

Matsumura, deceased et al.

[11] 4,363,802
[45] Dec. 14, 1982

[54] MORANOLINE DERIVATIVES

[75] Inventors: Shingo Matsumura, deceased, late of Kyoto, Japan, by Rumiko Matsumura, legal representative; Hiroshi Enomoto, Nagaokakyo, Japan; Yoshiaki Aoyagi; Yoji Ezure, both of Otsu, Japan; Yoshiaki Yoshikuni, Uji, Japan; Shigeaki Maruo; Nobutoshi Ojima, both of Kyoto, Japan; Kiyotaka Konno, Kyoto, Japan

[73] Assignee: Nippon Shinyaku Co. Ltd., Japan

[21] Appl. No.: 325,832

[22] Filed: Nov. 30, 1981

[30] Foreign Application Priority Data

Dec. 1, 1980 [JP] Japan ............................... 55-170009

[51] Int. Cl.³ ...................... A61K 31/70; C08B 37/00
[52] U.S. Cl. .................................. 424/180; 536/17.4
[58] Field of Search ........................... 536/18; 424/180

[56] References Cited

PUBLICATIONS

Yagi et al., Nippon Nogei Kagaku Kaishi, vol. 50, p. 571 (1976).

Primary Examiner—Alan Siegel
Attorney, Agent, or Firm—Jacobs & Jacobs

[57] ABSTRACT

Bisglucosyl moranoline of the formula (I)

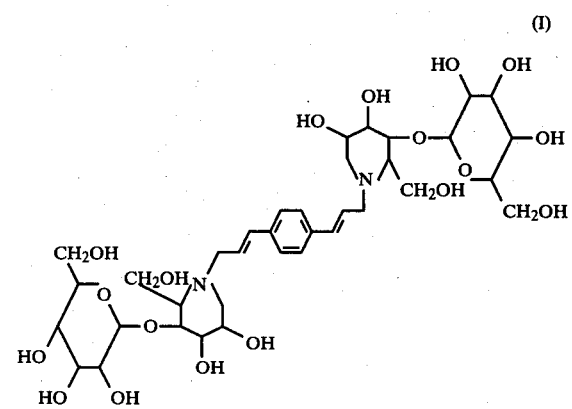

is useful in inhibiting increase of blood sugar in sugar-loaded animals and humans, and particularly for treatment of diabetes mellitus.

4 Claims, No Drawings

MORANOLINE DERIVATIVES

The present invention relates to a bisglucosyl moranoline derivative represented by the following structural formula (I), which is useful in the treatment of diabetes mellitus.

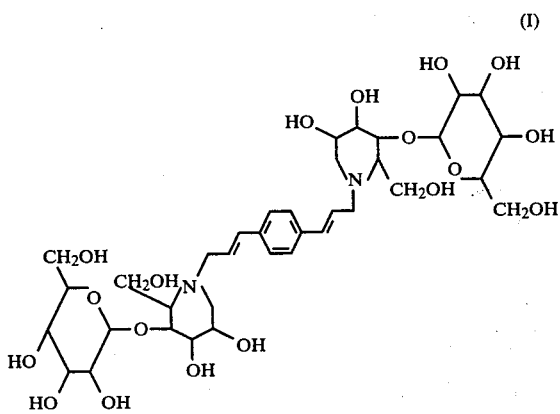

The present inventors have done extensive studies with the object of developing a safe and effective treatment of diabetes mellitus, and have found that the bisglucosyl moranoline derivative represented by the structural formula (I) exhibits marked inhibitory action against blood sugar increase when the blood is loaded with sugar.

Moranoline which is represented by the formula (II) below has been isolated from Mori Cortex (so-haku-hi) which is a crude drug of natural origin (cf. Yagi, et al., Nippon Nogei Kagaku Kaishi, volume 50, page 571, 1976 and Japanese Laid Open Patent Sho-52-83951):

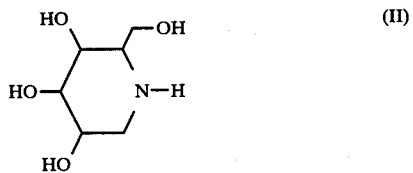

Subsequently moraniline (II) has been manufactured by fermentation using microorganisms belonging to genus Streptomyces (cf. Japanese Laid Open Patent Sho-54-84094).

Though moranoline (II) itself already exhibits inhibitory action against blood sugar increase in animals loaded with sugar, and is useful as a remedy for diabetes mellitus, derivatives having an improved effect have been discovered, namely 4-(alpha-D-glucosyl)-moranoline and 4-(alpha-D-glucosyl)-N-lower alkylmoranolines represented by the following structural formula (III), (cf. Japanese patent application Sho-54-159417 and Sho-55-76838):

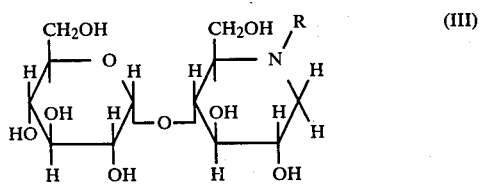

(where R stands for H or lower alkyl)

We have now found that the moranoline derivative (I) is far more potent than 4-(alpha-D-glucosyl)-moranoline (III) and 4-(alpha-D-glucosyl)-N-lower alkylmoranolines (III).

Inhibitory Action Against Blood Sugar Increase In Glucose-Loaded Rats

Each of four test compounds was administered orally in the dose specified in the table below together with 2 g/kg of sucrose to a group (each group consisting of four) of SD-strain male rats (five weeks age: body weights 100 to 120 grams). At constant time intervals, blood was collected from a tail vein until 180 minutes had elapsed from the administration of the test compound, and blood sugar levels were measured. The area ($\Delta AUC$) under the curve of time-blood sugar increase was measured for each of the four test compounds. In addition, water only was administered to one group of rats and sucrose only was administered to another group of rats. The area ($\Delta AUC$) obtained in the case where only water was administered is defined as "basal" and the area ($\Delta AUC$) where only sucrose was administered is defined as "control". The inhibitory ratio against blood sugar increase in each test group which was given a test compound is calculated by the following equation:

$$\text{Inhibitory Ratio} = \frac{(\Delta AUC \text{ of the control}) - (\Delta AUC \text{ of test group})}{(\Delta AUC \text{ of the control}) - (\Delta AUC \text{ of the basal})} \times 100$$

The inhibitory ratio calculated as above is given in the following table.

| COMPOUND TESTED | DOSE (mg/kg) | INHIBITORY RATIO |
|---|---|---|
| Moranoline (II) | 10 | 19% |
| 4-(alpha-D-Glucosyl)-moranoline | 10 | 44 |
| 4-(alpha-D-Glucosyl)-N—methyl-moranoline | 5 | 56 |
| Compound (I) | 1 | 65 |

Compound (I) is a novel substance which has not been reported in the literature, and can be synthesized by various routes. The most general way will be as follows. Thus, an activated derivative of bisallyl alcohol derivative of benzene such as, for example, bis (3-halo-1-propenyl)benzene represented by the following structure formula (IV):

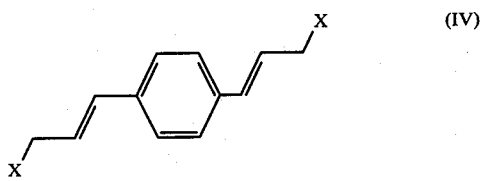

where X represents a halogen atom is made to react with 4-(alpha-D-glucosyl)-moranoline represented by the following structure formula (V) in a suitable solvent such as dimethyl sulfoxide in the presence of acid removing agents such as, for example, sodium carbonate or sodium bicarbonate.

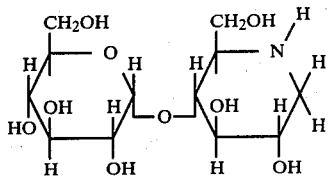

(V)

4-(alpha-D-Glucosyl)-moranoline can be prepared by a coupling of moranoline with alpha-cyclodextrine in the presence of cyclodextrine glucosyltransferase followed by the reaction of the resulting oligoglucosyl moranoline with glucoamylase after being adsorbed in strongly acidic ion exchange resin (cf. Japanese patent application Sho-55-131949).

Thus,

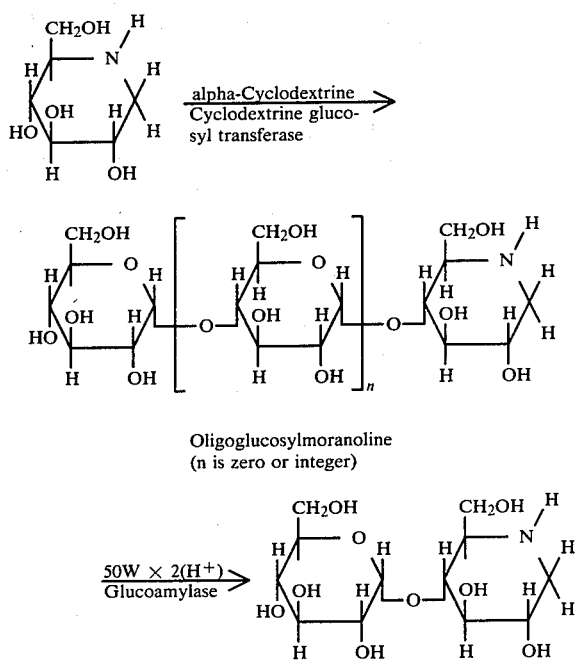

Oligoglucosylmoranoline
(n is zero or integer)

The method of making Compound (I) will be illustrated in the following example in more detail.

EXAMPLE (i) (Synthesis of benzene 1,4-bisallyl chloride)

Vinyl magnesium bromide prepared from 60 g of vinyl bromide and 14 g of metal magnesium was dissolved in tetrahydrofuran (abbreviated THF hereinafter) to prepare about 200 ml solution. After stirring, a solution of 25 g of terephthalaldehyde in 200 ml of THF was dropped therein during thirty minutes. After the dropping was completed, the reaction solution was stirred for thirty minutes more with stirring and refluxing. After cooled, small amount of water was added thereto with ice cooling so that the product was decomposed. To the reaction product was added ethyl acetate, insoluble matter was removed, the ethyl acetate layer was washed with water and concentrated to give 21 g of pale yellow and oily reaction product. The product was dissolved in 250 ml of ethyl acetate, 30 g of thionyl chloride was dropped therein with stirring, and heated to reflux for 2 hours after dropping. After cooled, the reaction mixture was evaporated to dryness under reduced pressure and the residual crystalline substance was recrystallized from small amount of ethyl acetate to give 15.8 g of benzene-1,4-bisallyl chloride, m.p. 124°–129° C.

(ii) Manufacture of 4-(alpha-D-Glucosyl)-moranoline (a) Culture of Bacillus macerans Erlenmeyer flask (500 ml volume) was charged with 150 ml culture broth (pH 7) consisting of 1% of corn steep liquor, 1% of soluble starch, 0.5% of ammonium sulfate, and 0.5% of calcium carbonate and was sterilized by heating at 120° C. for 15 minutes. Three platinum ears of Bacillus macerans IFO 3490 strain well grown on a slant medium consisting of 1% of peptone, 0.5% of yeast, 0.3% of glucose, 1.5% of glycerol, 0.3% of sodium chloride, 0.1% of liver powder (OXOID, a Registered Trade Mark for neutralized liver digest), and 1.5% of agar was inoculated and cultured at 37° C. for 3 days. The culture solution (300 ml) was inoculated in jar fermenter (15 liter volume) charged with 9 liters of the same medium composition and cultured at 37° C. for 3 days with enough aeration and stirring to give about 130–150 units (definition of the unit follows) of enzyme solution as a supernatant liquid after centrifugation.

(b) Unit of cyclodextrine glucosyl transferase activity

Soluble starch (0.7%) (product of Nakarai Kagaku Co.; for biochemical studies) was dissolved in 0.05 M acetate buffer (pH 5.5) and was used as a substrate solution. To 950 μl of the substrate was added 50 μl of the enzyme solution, the whole was made to react at 40° C. for 10 minutes, and the reaction was ceased by adding 0.5 ml of 0.5 N acetic acid. One hundred μl of the reaction solution was taken out and 3 ml of water and 0.8 ml of iodine solution in which iodine was dissolved so as to make 0.25 M KI solution 0.01 M, and the whole mixture was stirred and the absorbancy ($A_T$) was measured at 660 nm. Similarly 100 μl of the solution in which 50 μl of water and 0.5 ml of 0.5 N acetic acid were added to 950 μl of the substrate solution was taken out, iodine solution was added thereto, and the absorbancy ($A_R$) at 660 nm was measured. At this time, one unit is represented by an equation $$\text{One unit} = \frac{A_R - A_T}{A_R} \times 100 \times 2$$

and this corresponds to the activity where 1 ml of the enzyme solution cause 1% decrease in absorbancy within 1 minute at 40° C.

(c) Preparation of crude enzyme solution

Cultured solution of Bacillus macerans IFO 3490 was centrifuged and supernatant liquid was taken out. This was lyophilized then dissolved in small amount of water, and concentrated enzyme solution was obtained. This was well dialyzed at 5° C. against distilled water and the inner solution wherefrom lower molecular substances were removed was used as crude enzyme solution.

(d) Reaction and treatment

Then 6.5 g of moranoline was dissolved in small amount of water and the solution was adjusted to pH 5.7 with 3 N hydrochloric acid. After the pH adjustment, the volume was 32.5 ml. alpha-Cyclodextrine (26 g) was dissolved in 1300 ml of crude cyclodextrine glucosyl transferase enzyme solution (460 units/ml), an aqueous solution of moranoline was added thereto, and the mixture was adjusted to pH 5.67. This was shaken at 39° C.

for 3 days so that the reaction was carried out therein. The reaction solution was centrifuged, the supernatant liquid was passed through a column (volume of the resin: 50 ml) of Dowex 50 W×2 (H+) so that basic substances were adsorbed therein. After well washed with water, the resin was suspended in 1200 ml of water, 120 mg of alpah-1,4-glucanglucohydrase (about 22 units/mg) derived from Rhizopus niveus was added thereto, the mixture was incubated at 40° C., and the state of proceeding of the reaction was traced with an intermittent sampling followed by quantitative determination of glucose produced during the reaction. It was found that the amount of glucose increased rapidly after the reaction and, during the reaction for 5 hours, it reached at 89% of that of the end point. Reaction was further continued and, after 25 hours, the reaction was stopped. After the reaction, the resin was collected by filtration, well washed with water, eluted with 0.5 N ammonia water, the eluate was concentrated to dryness in vacuo, the resulting power was dissolved in small amount of water, passed through a column (12 cm$\phi$×30 cm) of Sephadex G-15, the desired fractions were collected, and dried by freezing to give 5.8 g of 4-(alpha-D-glucosyl)-moranoline, m.p. 138°–48° C. $[\alpha]_D^{24} = 121.6°$ (water).

(iii) Synthesis of the compound (I)

4-(alpha-D-Glucosyl)-moranoline (1 g) and 1 g of sodium bicarbonate were dissolved in 15 ml of dimethyl sulfoxide (abbreviated DMSO hereinafter) at 22°–24° C. and a solution of 380 mg benzene 1,4-bisallyl chloride in 15 ml of DMSO prepared with stirring was dropped therein during 60 minutes. The mixture was stirred at 22°–25° C. for 4 hours more. Then insoluble matter were removed by filtration, the filtrate was diluted with 300 ml of water, washed with chloroform, and passed through a column of Dowex 50 W×2 (H+) (20 ml). After the column was well washed with water, it was eluted with 0.2% ammonium water, and then the desired product was eluted with aqueous methanol containing 5% ammonia water. The eluate was evaporated to dryness in vacuo and the resulting crystals were recrystallized from 80% methanol to give 300 mg of the compound (I), m.p. 169°–173° C., $[\alpha]_{436}^{24} = -28.0°$ (water). Elementary analysis caulcuated for $C_{36}H_{56}O_{18}N_2 \cdot 2H_3O$: C 51.52%, H 7.15%, N 3.24%; Found: C 51.42%, H 7.20%, N 3.33%.

The moranoline derivative (I) of the invention is useful in the treatment of diabetes mellitus and as an agent in inhibiting blood sugar increase in sugar-loaded animals. The moranoline derivative (I) may be administered as such or in the form of a pharmaceutical composition to a human or animal in an amount effective to inhibit increase in blood sugar.

The pharmaceutical compositions of the present invention contain a major or minor amount e.g. 0.1% to 99.5%, preferably 0.5% to 90% of active ingredient as above defined in combination with a pharmaceutically acceptable, nontoxic, inert diluent or carrier, the carrier comprising one or more solid semi-solid or liquid diluent, filler and formulation adjuvant which is non-toxic, inert and pharmaceutically acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two, three, four or more single doses or, alternatively, one half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgement and considering the age, weight and condition of the recipient, the route of administration and the nature and gravity of the illness, generally the dosage will be from 0.1 to 300 mg of the moranoline derivative of the present invention, preferably 0.5 to 50 mg, per Kg of body weight per day. In some instances, a sufficient therapeutic effect can be obtained at a lower dose, while in others a larger dose will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsules is ingested.

Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and, optionally, with a binder such as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound.

Syrups can be prepared by dissolving the compound in a suitably flavored aqueous solution, while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccarin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

Rectal administration can be effected utilizing suppositories in which the compound is admixed with low-melting, water-soluble or insoluble solids such as polyethylene glycol, cocoa butter, higher esters as for example myristyl palmitate, or mixtures thereof.

While the routes of administration include oral, parenteral (i.e., intramuscular, intraperitoneal and intravenous), and rectal, oral administration is particularly preferred.

The preferred pharmaceutical compositions are therefore those in a form suitable for oral adminstration such as tablets and liquids.

What we claim is:

1. Bisglucosyl moranoline of the formula (I)

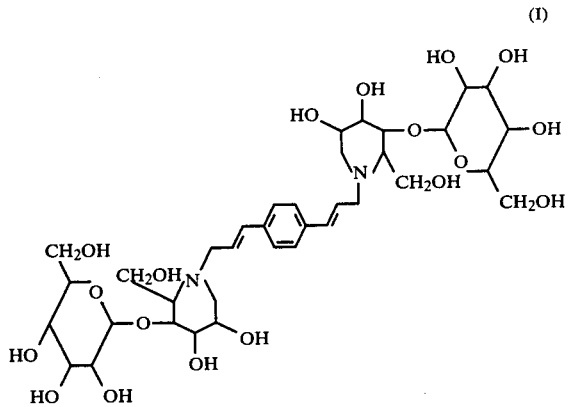

2. A pharmaceutical composition for inhibiting an increase in blood sugar, which comprises a blood sugar increase inhibiting an effective amount of the compound according to claim 1 and an inert pharmaceutically acceptable carrier or diluent therefor.

3. A method for inhibiting increase in blood sugar level in a sugar-loaded human or animal which comprises administering to said human or animal an amount of the compound according to claim 1 effective to inhibit increase in blood sugar.

4. A method of treating diabetes mellitus, which comprises administering to the sufferer an effective amount of the compound of claim 1.

* * * * *